(12) United States Patent
Stewart

(10) Patent No.: US 12,262,949 B2
(45) Date of Patent: Apr. 1, 2025

(54) EYE IMAGING

(71) Applicant: Konan Medical USA, Inc., Irvine, CA (US)

(72) Inventor: Charles Wm. Stewart, Dana Point, CA (US)

(73) Assignee: Konan Medical USA, Inc., Irvine, CA (US)

( * ) Notice: Subject to any disclaimer, the term of this patent is extended or adjusted under 35 U.S.C. 154(b) by 898 days.

(21) Appl. No.: 16/950,778

(22) Filed: Nov. 17, 2020

(65) Prior Publication Data

US 2021/0059514 A1  Mar. 4, 2021

Related U.S. Application Data

(63) Continuation-in-part of application No. PCT/US2019/068855, filed on Dec. 28, 2019.

(60) Provisional application No. 62/785,729, filed on Dec. 28, 2018.

(51) Int. Cl.
*A61B 3/14* (2006.01)
*A61B 3/00* (2006.01)
*G06V 10/25* (2022.01)
*G06V 40/19* (2022.01)
*G06V 40/60* (2022.01)

(52) U.S. Cl.
CPC .............. *A61B 3/14* (2013.01); *A61B 3/0008* (2013.01); *G06V 10/25* (2022.01); *G06V 40/19* (2022.01); *G06V 40/63* (2022.01)

(58) Field of Classification Search
CPC ......... A61B 3/14; A61B 3/0008; A61B 3/117; A61B 3/00; G06V 10/25; G06V 40/19; G06V 40/63; G06V 2201/03; G06V 40/60

USPC .................................................. 351/205–221
See application file for complete search history.

(56) References Cited

U.S. PATENT DOCUMENTS

| | | | |
|---|---|---|---|
| 7,744,216 B1* | 6/2010 | Uhlhorn .................. | G06F 21/32 351/204 |
| 2002/0097377 A1* | 7/2002 | Kudryashov ........ | A61B 3/1225 351/206 |
| 2002/0154269 A1* | 10/2002 | Liu .......................... | A61B 3/14 351/206 |
| 2003/0025876 A1 | 2/2003 | Nanjo | |

(Continued)

FOREIGN PATENT DOCUMENTS

| WO | 2012006330 A1 | 1/2012 |
|---|---|---|
| WO | 2018033727 A1 | 2/2018 |

OTHER PUBLICATIONS

International Application No. PCT/US2019/068855, International Search Report and Written Opinion, Mar. 27, 2020, 13 pages.

*Primary Examiner* — Thomas K Pham
*Assistant Examiner* — Kuei-Jen L Edenfield
(74) *Attorney, Agent, or Firm* — LaBatt, LLC

(57) ABSTRACT

A solution for imaging an eye of a patient is described. An illumination device can illuminate a linear volume of aqueous fluid of the eye of the patient with visible and/or infrared light from a location in a range between 25 to 65 degrees from a line of sight of the eye. At least one imaging device can acquire image data of the eye while it is being illuminated by the illumination device. The image data can be evaluated to determine one or more attributes of an aqueous fluid in an anterior segment of the eye delimited by the posterior surface of the cornea and the most anterior surfaces of the iris or lens and/or one or more attributes of the iris, eye, or surrounding tissues.

25 Claims, 4 Drawing Sheets

(56) References Cited

U.S. PATENT DOCUMENTS

| | | |
|---|---|---|
| 2005/0179867 A1 | 8/2005 | Suzuki et al. |
| 2009/0245594 A1 | 10/2009 | Abramovich et al. |
| 2010/0253907 A1 | 10/2010 | Korb et al. |
| 2013/0208245 A1* | 8/2013 | Campbell ............ A61B 3/0025 |
| | | 351/246 |

* cited by examiner

EYE IMAGING

REFERENCE TO RELATED APPLICATIONS

The current application is a continuation-in-part of International Application No. PCT/US2019/068855, filed on 28 Dec. 2019, which claims the benefit of U.S. Provisional Application No. 62/785,729, filed on 28 Dec. 2018, each of which is hereby incorporated by reference.

TECHNICAL FIELD

The disclosure relates generally to imaging an eye, and more particularly, to imaging an eye to evaluate a patient.

BACKGROUND ART

One or both eyes of an individual are commonly subjectively evaluated under visible light by an examiner, such as a medical practitioner. Alternatively, the examiner may capture images of the eye(s) to be evaluated by the examiner or alternate medical practitioner to determine one or more of: the presence, progression, severity, and/or the like, of a condition, such as a disease or disorder.

An illustrative condition is iritis or anterior uveitis, which is the inflammation of the iris and/or ciliary body. As part of an examination for iritis, an examiner can seek to determine the presence of and subjectively estimate the density of white blood cells in the anterior chamber of the eye within the aqueous (e.g., the portion of the eye located between the cornea and the iris). Additionally, the examiner can evaluate the eye for the presence of and subjectively estimate the density of flare, which is caused by the presence of protein molecules in the fluid within the anterior chamber.

To date, a slit lamp or "biomicroscope" is used to assist in evaluating an eye for the presence of various eye conditions, which can include white blood cells and/or flare. In particular, the slit lamp generates high-intensity visible light which is directed at the patient's eye and may be operator manipulated to create an optical section of various tissues and fluid-filled spaces. To evaluate inflammatory conditions of the eye, an examiner views the visible light-illuminated area(s) or volume(s) to make a subjective determination as to whether white blood cells and/or flare are present and, if so, estimate to what extent. Such examiner determinations are subject to various sources of error including: individual bias of visualized material; a dynamically moving field of cells; no precision controls on volume or other scene variables; etc.

Moreover, use of the slit lamp is typically uncomfortable for patients with specific eye diseases. For example, a patient frequently may be photophobic from ocular inflammation. In this case, the photophobic patient experiences significant discomfort while being exposed to the bright light required for the examiner to visualize microscopic cellular detail, rendering further difficulty in performing an accurate examination, e.g., due to uncontrolled eye and/or head movement by the patient, reflexive, uncontrolled blinking, etc.

SUMMARY OF THE INVENTION

Aspects of the invention provide a solution for imaging an eye and evaluating the eye using the image data. An embodiment of the invention provides a system comprising an illumination device configured to illuminate a linear volume of aqueous fluid of an eye of a patient. The illumination device can be located in a range between 25 to 65 degrees from a line of sight of the eye. The illumination device can project a beam of light, the dimensions of which can be mechanically and/or digitally constrained. The beam can be rectangular and can have a height and depth in a range between 100 to 3000 microns. The width can be bounded by an intersection with the cornea on the proximal aspect and the pupil, iris, and/or cornea, on the distal aspect. The beam of light can comprise infrared and/or visible light. The infrared light, which is generally invisible to both the operator and subject, can have a peak wavelength in a range between 750 to 850 nanometers. In a more particular example, the infrared light has a peak wavelength in a range between 800 to 850 nanometers. The visible light can comprise white light or light of a particular color, such as blue or green light. The illumination device can digitally constrain the third dimension, the planar area, which can be generally perpendicular to the axis of an imaging device, e.g., through software.

The system can further comprise at least one imaging device configured to acquire image data of the eye while being illuminated by the illumination device. The at least one imaging device can include at least one side imaging device having an imaging axis at approximately a ninety degree angle to the axis of the beam of light. The aqueous fluid imaged by the at least one side imaging device can be located behind a portion of the cornea located in front of the iris, e.g., the anterior chamber of the eye. The image data can be evaluated to determine one or more attributes of the eye, such as at least one of: a presence of an inflammatory process in the aqueous fluid in the anterior segment of the eye delimited by the posterior surface of the cornea and the most anterior surfaces of the iris or lens; a severity of the inflammatory process in the anterior chamber of the eye; or an effect of a drug/disease interaction in the eye as represented by a change in measured inflammatory processes and/or a change in the characteristic pigmentary appearance of the iris. Furthermore, the image data can be evaluated to determine a presence of a trauma and/or a disease.

At least one imaging device can comprise a high-resolution imaging device configured to acquire image data of the eye based on infrared and/or visible light. The at least one side imaging device can comprise a high-resolution imaging device oriented at an angle of approximately 90 degrees (e.g., within +/−15 degrees) to an axis of the rectilinear light projected by the illumination device. At least one additional imaging device can comprise a front imaging device located approximately coincident (e.g., within +/−15 degrees) with the line of sight of the examined eye, which can generate image data of some or all of the frontal aspect of the eye and/or surrounding tissues, including some or all of the anterior segment of the eye (e.g., the cornea, sclera, iris, and lens), the upper eyelid, lower eyelid, lacrimal caruncle, and/or the like, from infrared and/or visible light. The front imaging device can include a secondary front illumination device, which can illuminate some or all of the frontal aspect of the eye and/or surrounding tissues while it is being imaged by the front imaging device. The secondary front illumination device can illuminate the frontal aspect of the eye and/or surrounding tissues from generally the same location as that of the front imaging device.

An embodiment of the system can include a control system configured to operate the illumination device(s) and the at least one imaging device. The control system can be configured to process image data to determine one or more attributes of the eye. For example, the control system can generate and store a fingerprint of an iris pigmentation pattern of the eye, which can comprise a two-dimensional map of pigmentation densities and/or colors by processing image data acquired by the front imaging device. The fingerprint of the iris pigmentation pattern can include infrared visualized features of such pigmentation that are not seen by humans and are only apparent in the infrared image data. Additionally, the fingerprint of the iris pigmentation pattern can include features seen under visible light (e.g., one or more discrete wavelengths of visible light or white light), or a synthesis of infrared light as a heat signature (e.g., visible to the imaging device but not normally the human observer) and visible light (e.g., one or more selected wavelengths) visualized features. The control system can be configured to identify particles in at least one region of image data, such as image data acquired by the side imaging device, having sizes of at least 5 microns, e.g., in a range between 5 and 50 microns. The control system can determine a density of the particles and/or a distribution of counts of the particles in each of a plurality of sub-ranges of the range of particle sizes. The control system can be configured to calculate an average background luminance for at least one region of the image data without any particles or areas between particles, e.g., by digitally identifying and excluding particles from the calculation.

An embodiment of the system also can include one or more ambient sensors, which can acquire data regarding the ambient environment of the illumination device(s) and/or the imaging device(s). For example, the system can include at least one ambient light sensor, which can acquire data corresponding to an amount of ambient light present at one or more locations near the eye of the patient being illuminated and imaged or the room from which general lighting may provide extraneous ambient light to the patient's eye(s). The control system can process the data to determine a background luminance present. The control system can provide feedback to the user regarding the background luminance, such as indicating that the background luminance should be reduced, providing a level of the background luminance, and/or the like. Such feedback can be used to provide a consistency in examination imaging from time to time and subject to subject. The control system can account for the background luminance when evaluating the image data (e.g., calculating an average background luminance for the region(s) without any particles).

Other aspects of the invention provide methods, systems, program products, and methods of using and generating each, which include and/or implement some or all of the actions described herein. The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, aspects of the invention provide a solution for imaging an eye and evaluating the eye using the image data. An embodiment of the invention provides a system comprising an illumination device configured to illuminate a linear volume of aqueous fluid of an eye of a patient. The illumination device can be located in a range between 25 to 65 degrees from a line of sight of the eye. The illumination device can project a beam of light, the dimensions of which can be mechanically and/or digitally constrained. The system can further comprise at least one imaging device configured to acquire image data of the eye, e.g., while being illuminated by the illumination device. The aqueous fluid can be located behind a portion of the cornea located in front of the iris, e.g., the anterior chamber of the eye.

The image data can be evaluated to determine one or more attributes of the eye, such as at least one of: a presence of an inflammatory process in the aqueous fluid in the anterior segment of the eye delimited by the posterior surface of the cornea and the most anterior surfaces of the iris or lens; a severity of the inflammatory process in the anterior chamber of the eye; or an effect of a drug/disease interaction in the eye as represented by a change in measured inflammatory processes and/or a change in the characteristic pigmentary appearance of the iris. To this extent, the image data can be evaluated over time to assess change in an inflammatory process, which can indicate a potential success or failure of a therapeutic regimen. Furthermore, the image data can be evaluated to determine a presence of a trauma (e.g., surgical, accidental, etc., disruption of the cornea or sclera) and/or a disease (e.g., an autoimmune condition such as rheumatoid arthritis).

Further details are shown and described in conjunction with imaging and evaluating a human eye. However, it is understood that this is only illustrative and embodiments can be directed to imaging and/or evaluating an eye of any type of animal.

Figure 1:
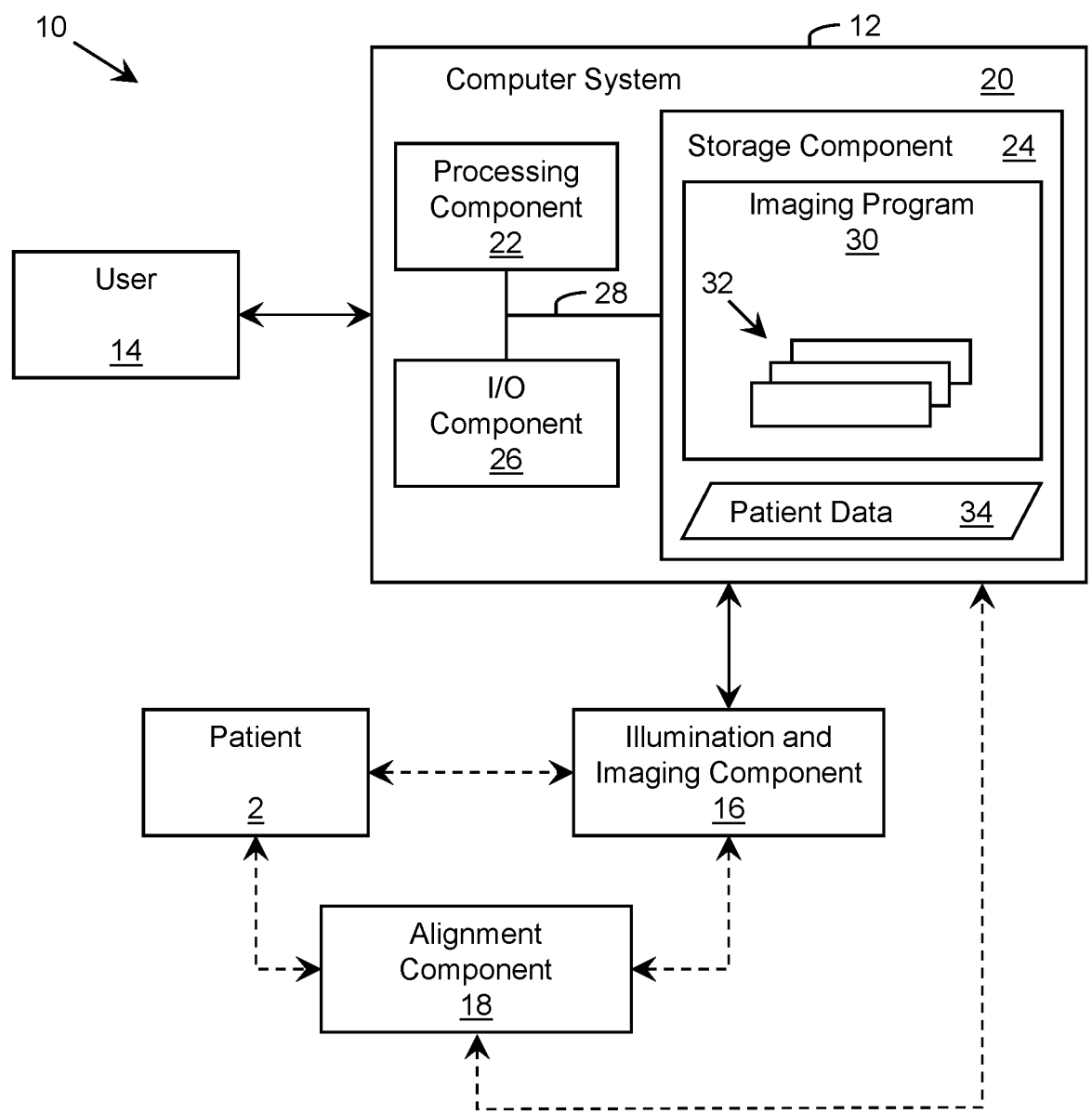
FIG. 1 shows an illustrative environment for acquiring image data of a patient according to an embodiment.

Turning to the drawings, FIG. 1 shows an illustrative environment 10 for acquiring image data of a patient 2 according to an embodiment. To this extent, the environment 10 includes a control system 12 that can perform a process described herein in order to acquire image data of a patient 2 by operating an illumination and imaging component 16 and/or an alignment component 18. In an illustrative embodiment, the control system 12 is implemented as a computer system 20 including an imaging program 30, which makes the computer system 20 operable to acquire image data of the patient 2, which can be stored as patient data 34, by performing a process described herein.

The computer system 20 is shown including a processing component 22 (e.g., one or more processors), a storage component 24 (e.g., a storage hierarchy), an input/output (I/O) component 26 (e.g., one or more I/O interfaces and/or devices), and a communications pathway 28. In general, the processing component 22 executes program code, such as the imaging program 30, which is at least partially fixed in the storage component 24. While executing program code, the processing component 22 can process data, which can result in reading and/or writing transformed data from/to the storage component 24 and/or the I/O component 26 for further processing. The pathway 28 provides a communications link between each of the components in the computer system 20.

The I/O component 26 can comprise one or more human I/O devices, which enable a human user 14 to interact with the computer system 20 and/or one or more communications devices to enable a system user 14 to communicate with the computer system 20 using any type of communications link. To this extent, the imaging program 30 can manage a set of interfaces (e.g., graphical user interface(s), application program interface, and/or the like) that enable human and/or system users 14 to interact with the imaging program 30. For example, an embodiment of the environment 10 can include a human practitioner 14 located in the same location as the patient 2 and operating the control system 12 via one or more user interfaces. In another embodiment of the environment 10, the control system 12 is operated remotely by a system user 14, which can communicate with the control system 12 via a network, such as the Internet. In this case, a practitioner can operate the system user 14 to control the control system 12 and/or send instructions to the patient 2 in order to acquire the patient data 34. Regardless, the imaging program 30 can manage (e.g., store, retrieve, create, manipulate, organize, present, etc.) the data, such as the patient data 34, using any solution.

The imaging program 30 can be implemented using a set of modules 32. In this case, a module 32 can enable the computer system 20 to perform a set of tasks used by the imaging program 30, and can be separately developed and/or implemented apart from other portions of the imaging program 30. As used herein, the term "component" means any configuration of hardware, with or without software, which implements the functionality described in conjunction therewith using any solution, while the term "module" means program code that enables a computer system 20 to implement the actions described in conjunction therewith using any solution. As used herein, it is understood that "program code" means any collection of instructions, in any language, code or notation, that cause a computing device having an information processing capability to perform a particular action either directly or after any combination of the following: (a) conversion to another language, code or notation; (b) reproduction in a different material form; and/or (c) decompression. To this extent, the imaging program 30 can be embodied as any combination of system software and/or application software.

The computer system 20 can comprise a single computing device, such as a general purpose computing article of manufacture (e.g., computing device) capable of executing program code, such as the imaging program 30, installed thereon. However, it is understood that a general purpose computing device executing the imaging program 30 is only representative of various possible equivalent computer systems that may perform a process described herein. To this extent, in other embodiments, the functionality provided by the control system 12 (e.g., the computer system 20 and the imaging program 30) can be at least partially implemented by one or more computing devices that include any combination of general and/or specific purpose hardware with or without program code. In each embodiment, the hardware and program code, if included, can be created using standard engineering and programming techniques, respectively.

In an embodiment, the computer system 20 comprises more than one computing device, each of which can comprise any of the various types of computing devices. In this case, a computing device can have only a portion of the imaging program 30 fixed thereon (e.g., one or more modules 32). Additionally, the computing devices can communicate with each other using one or more communications links. Furthermore, while performing a process described herein, the control system 12 can communicate with one or more other computer systems using one or more communications links. Each communications link can comprise any combination of various types of optical fiber, wired, wireless, etc., links; comprise any combination of one or more types of networks; utilize any combination of various types of transmission techniques and protocols; etc.

It is understood that two or more components, modules, and/or systems described herein may share some/all of their respective hardware and/or software. Furthermore, it is understood that some of the functionality discussed herein may not be implemented or additional functionality may be included in an embodiment of an environment 10.

As discussed herein, the control system 12 is configured to operate the illumination and imaging component 16 to acquire image data of a patient 2. In a more particular embodiment, the image data corresponds to one or both eyes of the patient 2. The control system 12 can store the image data as patient data 34, which can be presented to a user 14, such as a medical practitioner, for evaluating the patient 2. Additionally, the control system 12 can further process the image data to generate additional patient data 34, which can be utilized by the medical practitioner in evaluating the patient 2. In an embodiment described herein, the additional patient data 34 can include data corresponding to a presence of and/or density of white blood cells and/or a measure of a background luminance exclusive of (e.g., extracted from between) any identified particles in the anterior chamber of the eye.

In an embodiment, the control system 12 and/or the user 14 can assess the patient data 34 in one or more serial manners. For example, the control system 12 can acquire a sampling of a sequence of images collected at generally the same point in time (e.g., during a single office visit, before or after a treatment, and/or the like) for use in determining one or more attributes of the eye(s) of the patient 2. For example, the control system 12 can perform statistical averaging of the sequence of images to calculate, as examples, a statistical mean and/or a standard deviation for the number of white blood cells present in a defined sample volume, which can be stored as patient data 34 for the particular point in time. Similarly, the control system 12 can acquire a sampling of a sequence of images collected at two or more different points in time (e.g., multiple office visits on different days, such as weekly, or before and after a treatment in the same office visit), determine one or more attributes of the eye(s) of the patient 2 (e.g., by performing statistical averaging on each sequence of images), and store the attributes and image data as patient data 34 for each of the different points in time. The control system 12 can evaluate the patient data 34, e.g., the stored attributes, for the different points in time in a comparative manner to assess changes over time. The control system 12 and/or the user 14 can use the changes as a measure of a change in severity of a condition, an efficacy of a particular therapy to treat the condition, an effect of a treatment, and/or the like.

The patient data 34 can include various other data. For example, the patient data 34 can include data regarding the time and date on which the image data was acquired, identification information for the patient 2, a diagnosis for the patient 2, and/or the like. Such data can be included in a medical record for the patient 2, which can be subsequently reviewed and utilized in providing care for the patient 2.

To facilitate effective, repeatable imaging of patients 2, the environment 10 can further include an alignment component 18. The alignment component 18 can implement any type of solution for ensuring that the patient 2 is in proper alignment with the various devices of the illumination and imaging component 16 when the image data is acquired. Additionally, the alignment component 18 can implement any type of solution for ensuring that the various devices of the illumination and imaging component 16 are in proper alignment with each other when the image data is acquired. For example, the alignment component 18 can include a mounting structure on which the various devices of the illumination and imaging component 16 are mounted. Furthermore, the alignment component 18 can include structures and/or devices to assist in properly aligning the patient 2 for examination (e.g., a chin rest, laser alignment, and/or the like). As used herein, proper alignment means that the relative orientations and positions of the devices of the illumination and imaging component 16 and patient 2 are properly located within an acceptable margin of error for the evaluation. Such mounting and alignment structures are commonly utilized during eye evaluations. The alignment can be performed manually, e.g., by the user 14 moving a mechanical feature, and/or in an automated or semi-automated manner by the control system 12 controlling a motorized assembly. Illustrative mounting and alignment structures include manual, such as with tonometers on a biomicroscope, or automated, such as with autorefractors, autokeratometers, retinal cameras, and/or the like.

Figure 2:
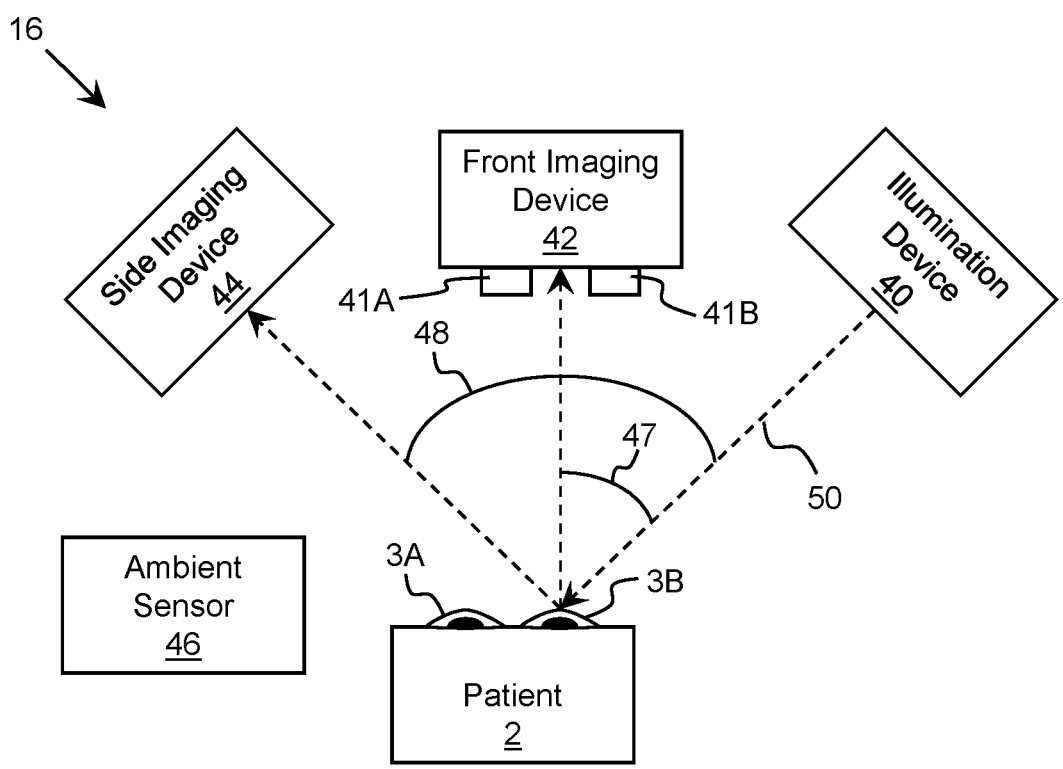
FIG. 2 shows an illustrative illumination and imaging component according to an embodiment.

FIG. 2 shows an illustrative illumination and imaging component 16 according to an embodiment. In this case, the illumination and imaging component 16 includes: an illumination device 40, which is configured to illuminate an eye 3A, 3B of the patient 2; a front imaging device 42, which is configured to acquire image data corresponding to a front view of the eye 3A, 3B of the patient 2 generally perpendicular to the plane of the iris; and a side imaging device 44, which is configured to acquire image data of the eye 3A, 3B of the patient 2 from an angle to the plane of the iris; and an ambient sensor 46, which is configured to acquire data regarding the ambient environment of the illumination and imaging component 16, e.g., the ambient illumination of the patient 2 environment.

Additionally, the illumination and imaging component 16 can include one or more secondary illumination devices 41A, 41B. For example, secondary illumination devices 41A, 41B can be configured to illuminate an eye 3A, 3B of the patient 2 from approximately the same alignment as the front imaging device 42. In an embodiment, the secondary illumination devices 41A, 41B can be physically attached to the front imaging device 42 and located in a fixed position with respect to the image sensor of the front imaging device 42. Alternatively, the secondary illumination devices 41A, 41B can be located separate from the front imaging device 42. Regardless, an embodiment of the illumination and imaging component 16 can include a plurality of secondary illumination devices 41A, 41B, which surround a lens for the front imaging device 42, e.g., in a circular array. The secondary illumination devices 41A, 41B can emit any type of light. In an embodiment, the secondary illumination devices 41A, 41B comprise a combination of white and/or colored (e.g., blue, green, etc.) visible light sources, such as light emitting diodes. In an embodiment, the control system 12 (FIG. 1) can be configured to selectively operate the secondary illumination devices 41A, 41B individually, in groups (e.g., sources of the same color), as a single group, and/or the like.

While not shown, it is understood that the various devices 40, 41A, 41B, 42, 44, 46 of the illumination and imaging component 16 can be mounted on a structure of an alignment component 18 (FIG. 1) that facilitates proper alignment of the orientations and positions of the devices 40, 41A, 41B, 42, 44, 46 with respect to each other and/or with respect to the patient 2 as described herein. Such a structure can enable manual movement of the devices 40, 41A, 41B, 42, 44, 46 and/or automatic or semi-automatic movement of one or more of the devices 40, 41A, 41B, 42, 44, 46 by the control system 12 (FIG. 1). In either case, the devices 40, 41A, 41B, 42, 44, 46 can be configured to be moved over various degrees of freedom (e.g., forward/backward, up/down, left/right, etc.) to accommodate patients 2 of varying sizes. In an embodiment, each of the devices 40, 41A, 41B, 42, 44 is moved to be approximately (e.g., within +/−15 degrees) laterally aligned with a height of the eyes 3A, 3B of the patient 2.

As illustrated, the front imaging device 42 and side imaging device 44 can acquire image data for one of the eyes, such as the eye 3B, at a time. However, it is understood that this is only illustrative. To this extent, in an embodiment, the illumination device 40 can be configured to illuminate both eyes 3A, 3B concurrently, and the front imaging device 42 and the side imaging device 44 can acquire image data for both eyes 3A, 3B concurrently. In this case, the illumination device 40 can include two light sources, each of which emits a separate beam of light as described herein. Similarly, the front imaging device 42 and/or the side imaging device 44 can include one or two cameras which can be operated to acquire the image data of both eyes 3A, 3B.

In general, the illumination device 40 can be located outside of the patient's 2 face on the same side as the eye 3B being illuminated. This configuration helps prevent the nose from interfering with the illumination, particularly at larger angles 47. To this extent, an embodiment of the illumination and imaging component 16 can include illumination devices 40 and side imaging devices 44 that are located on both sides of the patient 2. For example, a physical structure located on each side of patient 2 (e.g., where the illumination device 40 and the side imaging device 44 are shown) can include both a side imaging device 44 and an illumination device 40. Alternatively, the same illumination device 40 and side imaging device 44 can be used to illuminate and image both eyes 3A, 3B, e.g., after being relocated to the opposing side of the patient 2 or from the same approximate location on the same side of the patient 2 using an angle 47 for which the nose does not interfere.

Figure 3:
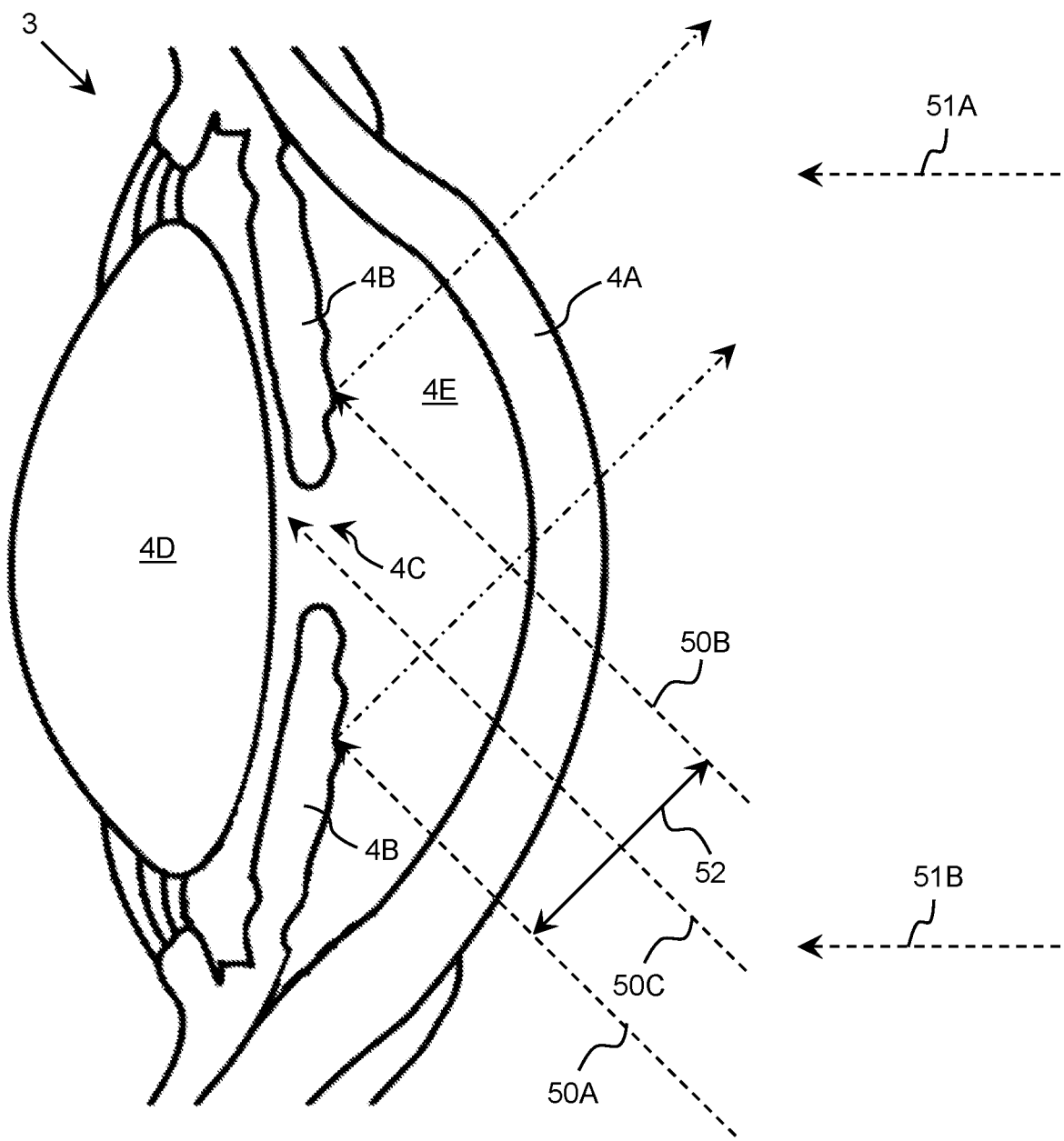
FIG. 3 shows a more detailed view of imaging an eye according to an embodiment.
Figure 4:
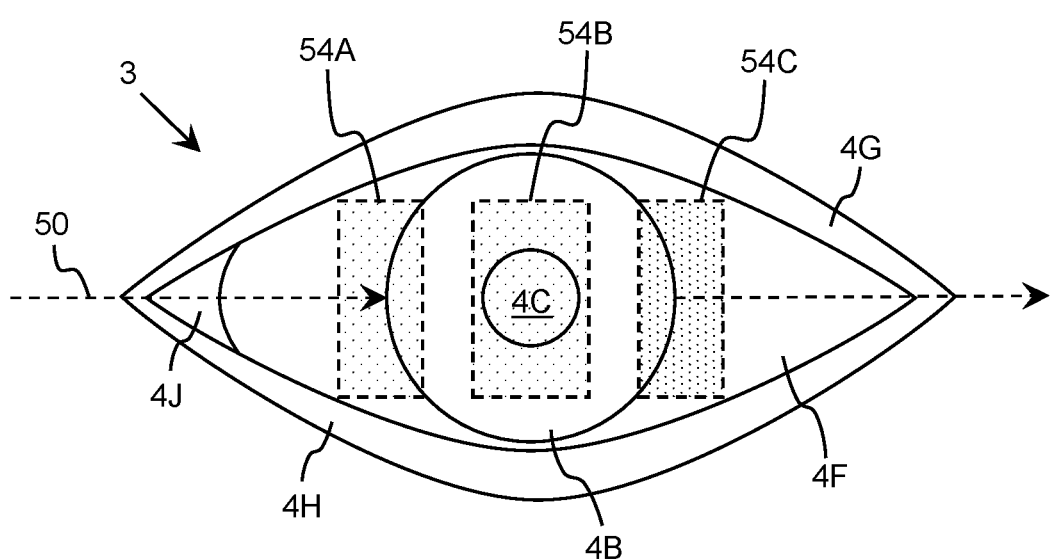
FIG. 4 shows an illustrative front view of imaging an eye according to an embodiment.

FIG. 3 shows a more detailed view of imaging an eye 3 according to an embodiment, while FIG. 4 shows an illustrative front view of imaging an eye according to an embodiment. Referring to FIGS. 3 and 4, as is known, a frontal aspect of an eye 3 includes an anterior segment, which includes a cornea 4A, an iris 4B, a lens 4D, and a sclera 4F (white of the eye). The iris 4B includes a pupil 4C, which the iris 4B constricts and dilates to adjust an amount of light that passes there through to the lens 4D. The cornea 4A and iris 4B define an anterior chamber 4E which includes an aqueous fluid. Additionally, the eye 3 is surrounded by various surrounding tissues. For example, such tissues include an upper eyelid 4G, a lower eyelid 4H, and a lacrimal caruncle 4J, and associated anatomical structures.

For a normal eye 3, the cornea 4A and the fluid in the anterior chamber 4E are clear, allowing substantially all light to pass through the aqueous without scatter to the iris 4B and/or the lens 4D. However, as discussed herein, the fluid in the anterior chamber 4E can include white blood cells and/or protein molecules due to immune system activity. The presence of such cells and/or molecules can be regarded as an urgent medical condition known commonly as intraocular inflammation, iritis, and anterior uveitis, which can adversely affect vision, and can be used to assess or grade a condition of a patient 2. Such inflammatory responses can occur from eye trauma, post-surgical complications from common surgeries such as for cataracts, and from autoimmune conditions such as rheumatoid arthritis.

Referring to FIGS. 2-4, in an embodiment, the patient 2 is directed to direct his/her line of sight directly toward the front imaging device 42 (e.g., at a light source, such as one of the illumination devices 41A, 41B). In this case, the illumination device 40 can illuminate the eye(s) 3A, 3B at an angle 47 to the line of sight for the patient 2. In an embodiment, the illumination angle 47 is between approximately 25 degrees and 65 degrees from the line of sight for the patient 2. The illumination device 40 can be configured to emit a beam of light 50 to illuminate a linear volume of the aqueous fluid in the anterior chamber 4E of the corresponding eye 3A, 3B. The beam of light 50 can have a predetermined set of attributes. Alternatively, one or more attributes of the beam of light 50, such as peak wavelength, dimensions, intensity, and/or the like, emitted by the illumination device 40 can be selectable, e.g., by a control system 12 (FIG. 1) and/or user 14 (FIG. 1). In either case, the illumination device 40 can mechanically and/or digitally constrain two dimensions of the volume of the aqueous fluid illuminated to control volumetric precision, e.g., by controlling the cross-sectional area of the beam of light 50.

As illustrated in FIG. 3, the secondary illumination device(s) 41A, 41B can emit a beam of light (e.g., a delimited by outermost portions of the beam 51A, 51B) from the front of the eye 3. The illumination device 40 and secondary illumination devices 41A, 41B can be operated to concurrently illuminate the eye 3 and/or illuminate the eye 3 at different times. The secondary illumination devices 41A, 41B can be configured to be operated similar to the illumination device 40. To this extent, the outermost portions of the beam 51A, 51B can impact the iris 4B on opposing sides of the pupil 4C. In an embodiment, the beam emitted by the secondary illumination devices 41A, 41B has an elliptical (e.g., circular) cross-section. Alternatively, the secondary illumination devices 41A, 41B can be operated to emit a diffuse beam of light that has an outer area that illuminates at least substantially all of the iris 4B of the eye 3. Still further, the secondary illumination devices 41A, 41B can be operated to emit a beam of light that illuminates some or all of the frontal aspect of the eye, including some of the sclera 4F, and/or some or all of the surrounding tissues, including the upper eyelid 4G, lower eyelid 4H, and/or lacrimal caruncle 4J.

In an embodiment, the illumination device 40 is configured to emit a beam of light 50 in the visible light spectrum. For example, the beam of light 50 can comprise a broad spectrum of wavelengths approximating white light. In an embodiment, the illumination device 40 can emit a beam of light 50 perceived as a particular color. For example, an embodiment of the beam of light 50 can comprise blue light having a peak wavelength between approximately 450 nanometers and 510 nanometers. Similarly, an embodiment of the beam of light 50 can comprise green light having a peak wavelength between approximately 495 nanometers and 570 nanometers. An embodiment of the secondary illumination devices 41A, 41B can be configured to emit visible light approximating white light and/or green or blue light.

In an embodiment, the illumination device 40 can emit a beam of light 50 that is not perceived by the patient 2. For example, the beam of light 50 can comprise infrared light, e.g., with a peak wavelength between 700 nanometers and 1000 nanometers. Infrared light can be used to reduce stimulation of the retina, thereby providing more comfort to a patient 2, e.g., a patient 2 having photophobic symptoms exaggerated by a disease condition, such as iritis or uveitis, during the examination process. In a more particular embodiment, the infrared light has a peak wavelength between 750 nanometers and 850 nanometers. In a still more particular embodiment, the infrared light has a peak wavelength between 800 nanometers and 850 nanometers. Infrared light in this range of wavelengths stimulate the retina of a human eye in a negligible manner. An embodiment of the secondary illumination devices 41A, 41B can include one or more light sources that emit infrared light.

In an embodiment, the beam of light 50 has a rectangular cross section. For example, as illustrated in FIG. 4, the beam of light 50 can intersect the cornea 4A of the eye 3 at an area 54A located on one side of the pupil 4C, intersect the iris 4B at an area 54B including at least some of the pupil 4C, and most of the light can exit the cornea 4A of the eye 3 at an area 54C located on the opposite side of the pupil 4C. In an embodiment, the rectangular cross section can have a height (as measured vertically perpendicular to the beam) in a range between approximately 500 microns and 3000 microns and depth (as measured laterally perpendicular to the beam) 52 in a range between approximately 100 microns and 2000 microns. In a more particular embodiment, the beam of light has a thin, rectilinear cross-section, e.g., with a height larger than a depth. In an embodiment, the height is 2-30 times greater than the depth. In a more particular embodiment, the height is 5-15 times greater than the depth. However, it is understood that the height and depth can be reversed in embodiments.

The illumination device 40 can be configured to enable selection of various heights and/or depths 52 and/or intensities for the beam of light 50, e.g., by a control system 12 and/or user 14. Regardless, the illumination device 40 can be configured to be aligned with the eye 3 such that the outermost portions of the beam 50A, 50B impact the iris 4B on opposing lateral and/or vertical sides of the pupil 4C and at least some of the beam 50C enters the pupil 4C and crosses in front of the pupil 4C. However, it is understood that this alignment is only illustrative and other configurations are possible. A length of the beam of light 50 within the eye 3, e.g., as delimited by a thickness of the cornea 4A on one aspect and the projected path through the pupil 4C or contacting the iris 4B on the opposite aspect, is in a range between approximately 2 millimeters to 10 millimeters. This length can be adjusted by, for example, adjusting the illumination angle 47 and/or a location on the eye 3 impacted by the beam of light 50.

The front imaging device 42 can acquire image data (e.g., video or a series of images) of the patient 2 and/or the eye(s) 3A, 3B, which can be presented to the user 14 to assist in gross positioning of the patient 2 with respect to the illumination device 40 and side imaging device 44. In an embodiment, the front imaging device 42 comprises a low magnification (e.g., 5× to 20×) imaging device. The front imaging device 42 can be located approximately (e.g., within +/−15 degrees) or substantially (e.g., within +/−5 degrees) coincident with the line of sight of the eye(s) 3A, 3B of the patient 2 being imaged. As a result, images of the eye(s) 3A, 3B acquired by the front imaging device 42 can be substantially perpendicular to a plane of the iris 4B. The front imaging device 42 can be sensitive to wavelengths corresponding to the beam of light 50 and/or the light emitted by the secondary illumination devices 41A, 41B. To this extent, the front imaging device 42 can comprise a camera that is sensitive to visible and/or infrared light.

In an embodiment, the control system 12 (FIG. 1) can use data acquired by one or more ambient sensors 46 to operate the illumination device 40, secondary illumination devices 41A, 41B, and/or imaging devices 42, 44, to acquire image data of the eye(s) 3A, 3B. For example, an illustrative ambient sensor 46 can comprise an ambient light sensor, which can acquire data corresponding to ambient illumination of the patient environment. In particular, the ambient sensor 46 can acquire data corresponding to a level of ambient light present at one or more locations near the patient 2, e.g., the eyes 3A, 3B of the patient 2, in the space around the patient 2, and/or the like. It is understood that ambient light refers to light that does not originate from the illumination and imaging component 16 (FIG. 1).

The control system 12 can process the ambient illumination data to determine a background luminance present. In an embodiment, the control system 12 can provide feedback to the user 14 regarding the background luminance, such as indicating that the background luminance should be reduced prior to imaging the eye(s) 3A, 3B. Furthermore, the control system 12 can present the user 14 with information indicating a level of the background luminance. In an embodiment, the control system 12 can prevent imaging of the eye(s) 3A, 3B from occurring until the background luminance is at or below a predetermined level. For example, the control system 12 can require that the background luminance be approximately zero (e.g., 1 candela per square meter or less) prior to imaging the eye(s) 3A, 3B. In this manner, the image data can have a defined baseline condition for evaluating the image data. For example, the image data can have a standardized background luminance visible from total light reflectivity measures of any proteins present in the image data.

In an embodiment, the control system 12 can account for the background luminance when evaluating the image data. For example, the control system 12 can account for any background luminance when calculating an average background luminance for the region(s) without any particles identified in the image data. To this extent, the control system 12 can acquire image data of the eye(s) 3A, 3B both without illumination by the illumination device 40 and with illumination by the illumination device 40 and use differences in the image data to evaluate the eye(s) 3A, 3B. In an embodiment, the control system 12 can adjust operation of the illumination device 40 and/or the secondary illumination devices 41A, 41B, e.g., to control total illumination at the eye(s) 3A, 3B. For example, the total illumination can be maintained at or below a predetermined maximum, within an acceptable range of a predetermined level (e.g., a level of illumination previously utilized), and/or the like.

In an embodiment, the front imaging device 42 acquires image data when the eye 3 is only illuminated by the secondary illumination devices 41A, 41B. The image data acquired by the front imaging device 42 can be stored as patient data 34. In an embodiment, the control system 12 (FIG. 1) can process one or more images of an eye 3A, 3B acquired by the front imaging device 42 to determine one or more attributes of the eye 3A, 3B. For example, the control system 12 can process the image data to generate a fingerprint of a pigmentation pattern for the iris 4B of an eye 3A, 3B. Similarly, the control system 12 can process the image data to identify cellular disrupted areas of the cornea or sclera. Such a fingerprint and/or disrupted area(s) can simultaneously include features that are both visible to the human eye and invisible to the human eye (e.g., from the infrared light image data).

The various patterns of iris pigmentation and heat signatures under infrared create a clear topographical map of the various pigmentation densities characterized by visible and infrared light. Certain drugs and disease interactions may affect the distribution of pigmentation density or the quantity or type of pigmentation and therefore be indicative of a change of condition or an adverse effect. The cellular disrupted areas can be indicative of an extent of trauma. The control system 12 can document changes to the pigmentation fingerprint and/or disrupted area(s) over time as imaged with consistent lighting scenes. Such changes can include infrared sensed changes that are invisible to both human observers and through standard imaging with cameras tuned or filtered for visible light spectrum imaging. These changes can be evaluated to determine an effectiveness of a treatment, a worsening/lessening of a condition, and/or the like.

In an embodiment, the control system 12 can acquire a series of images of the eye 3A, 3B using different illumination for each image. For example, the control system 12 can operate the secondary illumination devices 41A, 41B to illuminate the eye 3A, 3B using only infrared light, white light, or colored visible light (e.g., blue, green, etc.) during acquisition of each of the series of images. The control system 12 can evaluate some or all of the image data individually and/or synthesize the image data, e.g., non-visible image data or heat map data, with one or more visible light images, to create visual scenes that an examiner cannot otherwise visualize. For example, the control system 12 can evaluate the image data acquired using infrared illumination alone or synthesized with the image data acquired while illuminating with one or more of white light and/or colored visible light. The control system 12 and/or examiner can use the visual scenes to identify characteristic changes in pigmentation or appearance of the iris 4B.

In an illustrative embodiment, an examiner, such as the user 14, can apply one or more vital stains to one or both eyes 3A, 3B of the patient 2 prior to illuminating the eye(s) 3A, 3B with the secondary illumination devices 41A, 41B and acquiring image data of the eye(s) 3A, 3B using the front imaging device 42. The front imaging device 42 can acquire image data including a resulting staining pattern for the eye(s) 3A, 3B (e.g., the cornea 4A and surrounding eye structures). The staining pattern in the image data can enhance visualization aspects of the cellular disrupted areas of the cornea and/or sclera that take on the vital stain(s). For example, the staining pattern can add components to the image data that includes elements from infrared data that humans cannot see. In an embodiment, such image data can be acquired while the eye(s) 3A, 3B is (are each) illuminated by a beam of light 50 generated by the illumination device 40. The beam of light 50 and/or the light generated by the secondary illumination devices 41A, 41B can include, for example, visible and/or infrared light. In an embodiment, the light includes blue or green light and infrared light to enhance visibility of certain vital stains in the image data, which is generated based on a combination of the visible and infrared light.

In an embodiment, the side imaging device 44 acquires image data when the eye is only illuminated by the illumination device 40. The side imaging device 44 can acquire image data (e.g., video or a series of images) of the eye(s) 3A, 3B of the patient 2 at an angle 48 with respect to the beam of light 50. In an embodiment, the angle 48 is approximately ninety degrees (e.g., within +/−15 degrees). While the illumination device 40 and the side imaging device 44 are shown oriented at approximately the same angles (e.g., approximately forty-five degrees) with respect to the line of sight of the eyes 3A, 3B, it is understood that this is only illustrative and the relative orientations with respect to the line of sight of the eyes 3A, 3B can differ. Regardless, the side imaging device 44 can be sensitive to wavelengths corresponding to the beam of light 50. To this extent, the side imaging device 44 can comprise a camera that is sensitive to visible and/or infrared light.

In an embodiment, the side imaging device 44 comprises a high-resolution imaging device capable of resolving objects of 5 to 50 microns in diameter. In an embodiment, image data acquired by the side imaging device 44 can have sufficient resolution to identify individual particles present in the anterior chamber 4E of the eye(s) 3A, 3B having sizes as small as five microns. The image data acquired by the side imaging device 44 can include the pupil 4C. In this case, the pupil 4C can provide a dark background for a portion of the anterior chamber 4E in the image data, which can assist in evaluating the image data acquired by the side imaging device 44.

The image data acquired by the side imaging device 44 can be stored as patient data 34 and/or presented to an examiner, such as the user 14 for evaluation. For example, the image data can be analyzed to determine the presence of and/or density of white blood cells in the anterior chamber 4E. In an embodiment, the control system 12 can process at least a portion of the image data (e.g., the portion of the image data including the pupil 4C as a background) to determine one or more attributes of the eye 3A, 3B. For example, the control system 12 can identify all particles in one or more regions of the image data having a size between five and fifty microns, which corresponds to an expected size range for human white blood cells. From a number of such particles identified, the control system can calculate a density of the white blood cells. Additionally, the control system 12 can determine information corresponding to a distribution of sizes of the particles. For example, the control system 12 can identify the number and/or density of particles in each of a plurality of sub-ranges (e.g., sub-ranges of five microns each) of the five to fifty micron range. As used herein, a size of a particle corresponds to an average diameter of the particle in the image data.

The control system 12 also can evaluate one or more regions of the image data acquired by the side imaging device 44 that does not include any particles. For example, the control system 12 can identify region(s) of the imaged pupil 4C in which no particles are visible in the image data. To this extent, the control system 12 can identify the particles and digitally remove the corresponding areas from a region. Each region can have a regular or an irregular shape. Regardless, the control system 12 can calculate an average background luminance for the region(s). The average background luminance can provide a metric of the reflectance of proteins that may be present in the anterior chamber 4E, which corresponds to a presence of flare in the eye 3A, 3B, an indicator of an inflammatory process in the eye 3A, 3B.

The control system 12 can provide data regarding the identified particles (e.g., the number, density, distribution of sizes, etc.), average background luminance, and/or the like, for presentation to the user 14 and/or store the data as patient data 34. In an embodiment, the control system 12 can evaluate a series of rapid images acquired by the side imaging device 44 and calculate a representative value (e.g., average, median, and/or the like) of the quantities of white blood cells, densities of white blood cells, distributions of sizes of white blood cells, average background luminance, from the images, which can be used as the corresponding quantity, density, and distribution of sizes, of white blood cells and average background luminance for the eye 3A, 3B. For example, the control system 12 can individually analyze each of a series of thirty images acquired over a one second interval for cell density in the anterior chamber of the eye within the aqueous. However, it is understood that any number of images acquired over longer or shorter time durations can be utilized. For example, as few as a single image can be utilized. For multiple images, the time between images can correspond to a frame rate of the imaging device. However, the time between images can be a tenth of a second, a second, five seconds, or more, with the total time duration in which the images are acquired being five seconds, ten seconds, thirty seconds, or even a minute or more.

While shown and described herein as a method and system for imaging an eye, it is understood that aspects of the invention further provide various alternative embodiments. For example, in one embodiment, the invention provides a computer program fixed in at least one computer-readable medium, which when executed, enables a computer system to image an eye using an illumination and imaging component described herein and/or process the corresponding image data to determine one or more attributes of the eye. To this extent, the computer-readable medium includes program code, such as the imaging program 30 (FIG. 1), which enables a computer system to implement some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; and/or the like.

As used herein, unless otherwise noted, the term "set" means one or more (i.e., at least one) and the phrase "any solution" means any now known or later developed solution. The singular forms "a," "an," and "the" include the plural forms as well, unless the context clearly indicates otherwise. Additionally, the terms "comprises," "includes," "has," and related forms of each, when used in this specification, specify the presence of stated features, but do not preclude the presence or addition of one or more other features and/or groups thereof. It is understood that, unless otherwise specified, each value is approximate and each range of values included herein is inclusive of the end values defining the range. As used herein, unless otherwise noted, the term "approximately" is inclusive of values within +/− ten percent of the stated value, while the term "substantially" is inclusive of values within +/− five percent of the stated value.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A system comprising:
   a primary illumination device configured to illuminate a linear volume of aqueous fluid in an anterior chamber of an eye of a patient with a light;
   at least one imaging device configured to acquire an image data of the eye, the at least one imaging device including a primary imaging device configured to acquire a high-resolution image data of the illuminated linear volume of aqueous fluid in the anterior chamber of the eye, wherein the primary illumination device and the primary imaging device are oriented at an angle of approximately 90 degrees with respect to each other; and
   a control system configured to operate the primary illumination device to illuminate the eye, operate the primary imaging device to acquire the high-resolution image data while the eye is illuminated, and determine at least one attribute of the eye by identifying cells located within the illuminated linear volume of aqueous fluid in the anterior chamber of the eye which are visible in at least a portion of the high-resolution image data, wherein the high-resolution image data enables the control system to resolve cells in the linear volume of aqueous fluid in the anterior chamber of the eye as small as 5 microns in size which are visible in the image data.

2. The system of claim 1, wherein the primary illumination device projects a beam of light configured to impact an iris of the eye on opposing lateral and/or vertical sides of the pupil with at least some of the beam of light crossing in front of the pupil.

3. The system of claim 2, wherein the at least the portion of the high-resolution image data includes a region of the image data in which the illuminated linear volume of aqueous fluid in the anterior chamber of the eye and located in front of the pupil of the eye was imaged.

4. The system of claim 1, wherein the light comprises infrared light and the primary imaging device is sensitive to the infrared light.

5. The system of claim 1, wherein the primary imaging device is oriented in a range between 25 to 65 degrees from a line of sight of the eye.

6. The system of claim 1, wherein the at least one imaging device further comprises a secondary imaging device configured to acquire a secondary image data of the eye, wherein the secondary image data of the eye includes an image data of the cornea.

7. The system of claim 6, wherein the control system is further configured to process the secondary image data acquired by the secondary imaging device to determine a set of attributes of the eye.

8. The system of claim 7, further comprising a secondary illumination device configured to illuminate the eye with visible light of selected wavelengths, wherein the set of attributes of the eye comprise a staining pattern resulting from a vital stain made more visible by the visible light of selected wavelengths.

9. The system of claim 1, wherein the at least one attribute includes a number and/or a density of cells located in at least one region of the high-resolution image data.

10. The system of claim 9, wherein the number and/or the density of cells corresponds to only cells having sizes between 5 and 50 microns.

11. The system of claim 1, wherein the at least one attribute includes, for each of a plurality of sub-ranges of a range of 5 to 50 microns, a number and/or a density of cells present in at least one region of the high-resolution image data with a size within the corresponding sub-range.

12. The system of claim 1, wherein the at least one attribute includes an average background luminance for at least one region of the high-resolution image data extracted from between any identified cells.

13. The system of claim 1, further comprising at least one ambient light sensor configured to acquire data corresponding to an amount of ambient light present at least at one location near the eye of the patient being imaged or in an area surrounding the patient, wherein the control system is configured to determine a background luminance using the data acquired by the at least one ambient light sensor.

14. The system of claim 1, wherein the illuminated linear volume of aqueous fluid of the eye has a height and depth in a range between 100 microns and 3000 microns.

15. The system of claim 1, wherein the control system is configured to calculate at least one volumetric measurement based on the identified cells to determine the at least one attribute of the eye.

16. The system of claim 1, wherein the primary illumination device is configured to project a beam of light configured to illuminate a known depth of the linear volume of aqueous fluid of the eye.

17. The system of claim 1, wherein at least one dimension of the illuminated linear volume of aqueous fluid of the eye is digitally constrained.

18. The system of claim 1, wherein the primary illumination device generates an infrared light, and the primary imaging device acquires an infrared-based high-resolution image data.

19. A system comprising:
    a primary illumination device configured to illuminate a linear volume of aqueous fluid in an anterior chamber of an eye of a patient with a light; and
    a primary imaging device configured to acquire a high-resolution image data of the illuminated linear volume of aqueous fluid in the anterior chamber of the eye, wherein the primary illumination device and the primary imaging device are oriented at an angle of approximately 90 degrees with respect to each other;
    a secondary imaging device configured to acquire a secondary image data of the eye; and
    a control system configured to operate the primary illumination device to illuminate the eye, operate the primary imaging device to acquire high-resolution image data while the eye is illuminated, operate the secondary imaging device to acquire the secondary image data of the eye, and determine at least one attribute of the eye by identifying cells located within the illuminated linear volume of aqueous fluid in the anterior chamber of the eye which are visible in at least a portion of the high-resolution image data acquired by the primary imaging device, wherein the high-resolution image data enables the control system to resolve cells in the linear volume of aqueous fluid in the anterior chamber of the eye as small as 5 microns in size which are visible in the image data.

20. The system of claim 19, wherein the at least one attribute includes a number and/or a density of cells having sizes between 5 and 50 microns, which are located in at least one region of the high-resolution image data.

21. The system of claim 19, wherein the at least one attribute includes an average background luminance for at least one region of the high-resolution image data extracted from between any identified cells.

22. The system of claim 19, wherein the control system is further configured to process the secondary image data acquired by the secondary imaging device to determine a set of attributes of the eye, wherein the secondary image data of the eye includes an image data of the cornea.

23. A method of determining an attribute of an eye, the method comprising:

generating light from a primary illumination device to illuminate a linear volume of aqueous fluid in an anterior chamber of an eye of a patient with a light;

acquiring, with a primary imaging device, a high-resolution image data of the illuminated linear volume of aqueous fluid of the eye while the eye is being illuminated by the primary illumination device, wherein the primary illumination device and the primary imaging device are oriented at an angle of approximately 90 degrees with respect to each other; and a control system determining an attribute of the eye by identifying cells located within the illuminated linear volume of aqueous fluid in the anterior chamber of the eye which are visible in at least a portion of the high-resolution image data, wherein the high-resolution image data enables the control system to resolve cells in the linear volume of aqueous fluid in the anterior chamber of the eye as small as 5 microns in size which are visible in the image data.

24. The method of claim 23, further comprising:

acquiring, with a secondary imaging device, a secondary image data of the eye; and the control system processing the secondary image data acquired by the secondary imaging device to determine a set of attributes of the eye.

25. The method of claim 24, further comprising generating visible light of selected wavelengths from a secondary illumination device to illuminate the eye, wherein the eye is illuminated with the visible light of selected wavelengths when the secondary image data is acquired.

\* \* \* \* \*